United States Patent [19]

Van Wijnendaele et al.

[11] Patent Number: 4,683,294

[45] Date of Patent: Jul. 28, 1987

[54] PROCESS FOR THE EXTRACTION AND PURIFICATION OF PROTEINS FROM CULTURE MEDIA PRODUCING THEM

[75] Inventors: Frans Van Wijnendaele, Ottenburg; Daniel Gilles, Genval; Guy Simonet, Perwez, all of Belgium

[73] Assignee: Smith Kline RIT, S.A., Belgium

[21] Appl. No.: 719,601

[22] Filed: Apr. 3, 1985

[51] Int. Cl.$^4$ .............................................. A61K 39/12
[52] U.S. Cl. ................................... 530/371; 424/88; 424/89; 530/414; 530/419; 530/420; 530/421; 530/424; 530/806
[58] Field of Search ....................... 260/112 R, 112 B; 424/89, 88; 530/371, 414, 421, 419, 420, 424, 806

[56] References Cited

U.S. PATENT DOCUMENTS

| | | |
|---|---|---|
| 3,790,552 | 2/1974 | Johnson et al. |
| 3,951,937 | 4/1976 | Vnek et al. |
| 3,994,879 | 11/1976 | Neurath et al. |
| 4,096,136 | 6/1978 | Ayers et al. ............... 424/101 X |
| 4,118,478 | 10/1978 | Prince et al. ............... 424/89 X |
| 4,206,014 | 6/1980 | Reichert et al. ............ 424/89 |
| 4,335,214 | 6/1982 | Adamowicz et al. ...... 424/89 X |
| 4,349,539 | 9/1982 | Wampler .................... 424/89 |
| 4,379,087 | 4/1983 | Coan et al. |
| 4,542,016 | 9/1985 | Trepo ........................ 424/89 X |
| 4,554,157 | 11/1985 | Skelly et al. ............... 424/89 |
| 4,558,011 | 12/1985 | Brzosko et al. ............ 424/89 X |
| 4,565,697 | 1/1986 | Ohmura et al. ............ 424/89 |

FOREIGN PATENT DOCUMENTS

A-103409  3/1984  European Pat. Off.
A-106828  4/1984  European Pat. Off.
A-112506  7/1984  European Pat. Off.

OTHER PUBLICATIONS

Hitzeman et al., *Nucl. Acids Res.* 11:2745 (1983).
Burstein et al., *Adv. Lip. Res.* 11:67 (1973).
Van Dalen et al., *Biochim. Biophys. Acta* 147:421 (1967).
Derwent Patent Abstract 84–217127/35.
Funakoshi et al., *Prog. Med. Virol.* 27:163 (1981).
Ingham, *Meth. Enzym.* 104:351 (1984).
*Biochim. Biophys. Acta,* 317 (1973) 505–516, Foster et al.
*Folia Microbiol.* 23, 88–96 (1978), B. P. Vajda.
*Biochim. Biophys. Acta,* 82 (1964) 463–475, Polson et al.
*Archio Virusforsch.* 42, 303–306 (1973), G. J. Lancz.
*Anal. Biochim.* 72, 502–512 (1976), Honig et al.
*J. Biol. Chem.,* 256, No. 18, 9750–9754 (1984), Staehelin et al.
*Proc. Int. Symp.,* No. 18, 37–49 (1981), Adamowicz et al.

*Primary Examiner*—Howard E. Schain
*Attorney, Agent, or Firm*—Carol G. Canter; Janice E. Williams; Alan D. Lourie

[57] ABSTRACT

The process is applicable to the supernatant of engineered yeast cells disrupted in the presence of a non-ionic detergent: it comprises the precipitation of contaminants by polyethylene glycol and the treatment cation or, after eventual ultrafiltration, with ammonium sulfate.

18 Claims, No Drawings

PROCESS FOR THE EXTRACTION AND PURIFICATION OF PROTEINS FROM CULTURE MEDIA PRODUCING THEM

FIELD OF THE INVENTION

The invention relates to an improved process for the extraction and purification of proteins from culture media producing them; more particularly, the process relates to the extraction and purification of hepatitis B virus surface antigen and alpha-1-antitrypsin produced by recombinant DNA technique in engineered cell cultures, more particularly engineered yeast strains cultures.

BACKGROUND OF THE INVENTION

Different microorganisms, among which bacteria and yeasts can be used as host organisms for different plasmids containing a DNA molecule comprising a nucleotide sequence coding for a specific protein. Among these microorganisms, yeasts are presently preferred and currently used. For example, European Patent application publication No. 0 106 828 discloses the use of Saccharomyces cerevisiae strains for the production of hepatitis B virus surface antigen (HBsAg) and European Patent application publication No. 0 103 409 relates to the production of alpha-1-antitrypsin from yeast plasmids.

Protein production in yeast strains indeed presents substantial advantages over production in bacterial strains. These advantages result from the rather easy growth of yeasts in large scale fermentors and from the fact that, contrary to bacteria, yeasts do appear to ressemble mammalian cells in their capacity to add carbohydrate groups to newly synthesized proteins.

Nevertheless the extraction and purification of the protein from a yeast culture do present technical problems due to the rather complex chemical composition of the yeast cell and more particularly to the presence of high lipid levels when the yeast growth is extended in order to improve the polypeptide production yield.

For example, the Saccharomyces cell wall is thought to consist of 3 layers: (a) an inner layer of alkali-insoluble $\beta$-glucan, (b) a middle layer of alkali-soluble $\beta$-glucan and (c) an outer layer of glycoprotein in which the carbohydrate consists of phosphorylated mannan; beneath the cell wall is a cytoplasmic membrane consisting of a very complex mixture of neutral lipids (mono-, di- and tri-glycerides), free and esterified sterols, a complex sphingolipid, glycerophosphatides and neutral as well as acidic glycolipids; the nucleus contains DNA, various species of RNA and a polyphosphate; vacuoles may contain a great variety of components of both high and low molecular weights, they serve as storage vesicles for a number of hydrolytic enzymes; the mitochondria are rich in lipid, phospholipid and ergosterol components of the membrane system and the cytoplasm contains a.o. large quantities of ribosomes, polyphosphates, glycogen and a number of glycolytic enzymes. Most yeast cells (such as Saccharomyces species) also contain some amount of lipid in the form of globules the amount of which does increase in extended cultures.

A number of multi-steps processes have been disclosed for the extraction and purification of proteins from different sources. Examples referring to proteins produced by engineered microorganisms are those published by Th. STAEHELIN et al. (J. Biol. Chem. 256; 9750-54; 198), K. MURRAY et al. (The EMBO J. 3; p. 645-650; 1984) and R. A. HITZEMAN et al. (Nucl. Ac. Res. 11; 2745-2763; 1983).

Typically, when the produced protein is cell bound, those different processes involve 3 series of steps.

In the first series of steps, the desired protein is removed from the cell interior. Therefore, the cells are either lysed (e.g. by enzymatic treatment) or disrupted (e.g. by mechanical forces (such as shearing forces (e.g. X-press or French press) or shaking with glass beads, eventually with addition of a detergent (see for instance K. MURRAY et al. loc. cit. and R. A. HITZEMAN et al. loc. cit.).

In the second series of steps, the medium is enriched in desired protein, e.g. by fractional precipitation by addition of ammonium sulfate and/or in the presence of polyethylene glycol.

Finally, in the third series of steps, substantially all contaminants are eliminated from the medium, e.g. by one or several operations selected from the group comprising ultrafiltration, ion exchange, gel filtration chromatography and isopycnic gradient centrifugation.

In such process, it is obvious that contaminants like accompanying proteins (cited by R. A. HITZEMANN et al. loc. cit.), nucleic acids and lipids and more particularly high lipid levels have a harmful influence on at least one of the steps of the third series (e.g. ultrafiltration and column chromatography) and the proteolytic enzymes must be eliminated rapidly from the medium. Moreover, it has also been noticed that ammonium sulfate precipitation is not possible without a previous rough delipidation because lipids interfere with this precipitation.

Therefore, it is of prime importance to dispose of a method wherein most of the contaminants are eliminated before the third series of steps.

Some among the previously described processes disclose the use of polyethylene glycol as a selective precipitating agent for proteins and a method for the precipitation of lipoproteins from plasma by using lipoprotein-polyanion-metal interactions has also been reported.

The method for fractional precipitation of proteins by using nonionic water-soluble polymers, in particular polyethylene glycol (PEG) has been introduced by POLSON et al. (Biochem. Biophys. Acta 82; 463-475; 1964) and discussed by different authors. Among them W. HONIG et al. (Analyt. Biochem. 72; 502-512; 1976) mention that "the specificity of precipitation, that is the ratio of desired protein and total protein, can be improved by using PEG fractions of lower average molecular weight than the generally employed PEG 6000". Nevertheless although "by manipulation of pH concentrates of individual plasma proteins may be obtained" the authors added "however, purification of more complex protein mixtures such as the supernatant of a cell homogenate is considerably poorer".

P. R. FOSTER et al. (Biochim. Biophys. Acta 317; 505-516; 1973 have described a method for the precipitation of enzymes from cell extracts of Saccharomyces cerevisiae by PEG. Methods for the concentration and purification of viruses and bacteriophages with PEG have been disclosed by B. P. VAJDA (Folia Microbiol. 23, 88-96; 1978) and G. J. LANCZ (Arch. Virusforsch. 42; 303-306; 1973). In the field of hepatitis antigen isolation, the purification of hepatitis B surface antigen (HBsAg) by a method comprising two successive treatments with PEG 6000 has been described by Ph. ADA- MOWICZ et al. (p. 37-49 INSERM SYMPOSIUM No. 18, HEPATITIS B VACCINE, Publ. ELSEVIER, Amsterdam, Holland, 1981). In this method of HBsAg purification from plasma, immune complexes and most of the lipoproteins are, in a first step, precipitated from serum by PEG 6000 at a concentration of 5.5% and, in a second step, HBsAg is precipitated from the isolated supernatant by addition of PEG at a final concentration of 10%.

In the patent literature,

U.S. Pat. No. 3,790,552 discloses a method for removing hepatitis-associated antigen from a protein fraction which comprises a step wherein PEG having a molecular weight 200–6,000 is used in an amount of 12–30% (w/v) for precipitating said antigen.

U.S. Pat. No. 3,951,937 discloses a process for the purification of hepatitis B antigen (HBAg) involving a double precipitation of HBAg with PEG (4.0–4.5 weight percent) having a molecular weight of at least 600.

U.S. Pat. No. 3,994,870 discloses a method for purifying hepatitis B antigen (HBAg) wherein HBAg is precipitated by addition of 4.0–4.5 weight percent PEG and thereafter subjected to affinity chromatography utilizing insoluble concavalin A as a chromatographic adsorbent.

European patent application, publication No. 0 112 506 discloses a process for producing a hepatitis B infection preventing vaccine from plasma comprising ammonium sulfate precipitation followed by adsorption on colloidal silicate and two successive precipitation steps with PEG (having a molecular weight of 2,000–10,000) at a 3–7% (w/v) to precipitate hepatitis B virus and immune complexes and at a 15–20% (w/v) in the supernatant to precipitate HBsAg.

In the field of alpha-1-antitrypsin isolation, Japanese patent application No. 9128-335 (Derwent abstract 84-217127) discloses the precipitation of alpha-1-antitrypsin from plasma fraction by addition of PEG in an amount of 15–20% (w/v).

As mentioned above, a method for the precipitation of lipoproteins by using lipoprotein-polyanion-metal interactions has also been previously reported (for instance: M. BURSTEIN et al. Adv. Lip. Res. 11; 67–108; 1973 and A. VAN DALEN et al. Biochim. et Biophys. Acta 147; 421–427; 1967). This method is performed by interaction between the lipoproteins, a bivalent metal cation and an acidic polysaccharide and, in these operative conditions, the amount of precipitate is a function of the bivalent metal cation concentration in the medium.

DESCRIPTION OF THE INVENTION

The starting material for the process of this invention (herein also referred to as 'crude extract') is the supernatant of engineered yeast cells having produced a cell-bound protein and disrupted in the presence of a nonionic detergent, as well known in the art.

According to the present invention, there is then made a combination of the fractional precipitation by PEG (hereafter refered to as first step) followed by either a fractional precipitation by polyvalent metal cation (more particularly bivalent metal such as calcium and manganese) or by ammonium sulfate treatment, said ammonium sulfate treatment being eventually preceded by ultrafiltration of the supernatant from the first step.

The present invention derived from the discovery that, when solid PEG (e.g. PEG 6000) is employed at a concentration of 6–12% (w/v) for the extraction of HBsAg from engineered yeast cells disrupted in the presence of a nonionic detergent, HBsAb does not precipitate. Moreover, by subsequent addition of ammonium sulfate, a two phase system is formed which is characterized by the fact that the HBsAg is present in the PEG phase while most contaminants are in the aqueous phase. This result is surprising because, according to the general teaching of the prior art in other crude media, these operative conditions should provoke the precipitation of the BHsAg. Thus, it is a first object of the present invention to use PEG as a solvent for the desired protein produced by yeast cell cultures whereas most of the contaminants are eliminated by precipitation from the medium.

According to molecular weight, PEG does exist either in solid form or in liquid form, the frontier between both forms being around a molecular weight of 1500.

In the first step of the process according to the invention (which could also be considered as a clarification step), PEGs having different molecular weights can obviously be used with adequate concentration adjustment according to the corresponding molecular weight.

For instance, the PEG concentration is preferably 6 to 12% (w/v) when using solid PEG (e.g. PEG 6000) and from 10 to 35% (v/v)—and preferably from 20 to 30% (v/v) when liquid PEG (e.g. PEG 300 or 400) is employed. Nevertheless, the use of liquid PEG is preferred for technical reasons among which the easiness of later ultrafiltration.

Thus, according to the invention, there is provided a process for the extraction and purification of proteins, more particularly HBsAg or alpha-1-antitrypsin, from the supernatant of yeast cells disrupted in the presence of a nonionic detergent (preferably a polysorbate detergent), said supernatant being herein referred to as 'crude extract', which method comprises a first step wherein either 6–12% (w/v) of solid PEG or preferably 10–25% (v/v) of liquid PEG is added to the crude extract brought to pH 6 (±0.1), the above limits of PEG concentrations being mainly fixed by the point at which clarification is reached since further addition of PEG has only detrimental effects, i.e. higher viscosity of the medium and risk of undesired co-precipitation of HBsAg or alpha-1-antitrypsin.

In the process of the invention, PEG is regarded as a polymerized organic solvent favouring a.o. the precipitation of the (lipo)proteins whose isoelectric point is close to pH 6 and the solubilisation of the other (lipo)proteins, i.e. those which have a markedly different isoelectric point and those which are highly hydrophobic.

It has been noticed that this PEG clarification step precipitates about 75% of the contaminant proteins, 90% of the polysaccharides, 94% of the nucleic acids and 45% of the lipids, while substantially the whole HBsAg or alpha-1-antitrypsin content is recovered in the supernatant.

As indicated hereinabove, the present invention includes a combination of steps, the first one of them being a clarification step, to yield a partly purified and eventually somewhat opalescent solution of the desired protein.

In the second step of the process of the invention, the obtained partly purified solution is either treated with a polyvalent—more particularly bivalent—metal cation such as an aqueous solution of calcium or manganese chloride at a final concentration of 30 mM or treated with ammonium sulfate and this ammonium sulfate treatment is performed either after ultrafiltration of the opalescent solution by addition of solid ammonium sulfate up to 40-50% saturation, according to the classical salting out method to precipitate the desired protein which can be taken over in a phosphate buffer or by addition of ammonium sulfate up to 40-50% saturation to the PEG containing supernatant, forming a two-phase system with the desired protein in the PEG phase.

Each of these variations for the second series of steps does provide a clear solution of the desired protein substantially purified regarding its polysaccharides, nucleic acids, lipids and contaminant proteins content.

The so-obtained solution can then be processed in the above defined classical third series of steps, e.g. eventual ultrafiltration, gel filtration and column chromatography and, in a preferred embodiment of the present invention, this third series of steps comprises successively an ultrafiltration, a first gel filtration, a column chromatography on weakly alkaline anion exchanger with diethylaminoethyl (DEAE) groups and a second gel filtration to yield a highly purified HBsAg or alpha-1-antitrypsin solution suitable for medical use.

When tested by SDS PAGE polyacrylamide gel electrophoresis, the product recovered after the second gel permeation is shown to be more than 90% pure with regard to the 23K band which is characteristic of HBsAg of yeast origin.

Thus, the primary advantage of the method of this invention is that it does remove substantially all polysaccharides, nucleic acids, lipids and proteinaceous material and another advantage of the invention is that the desired protein may finally be separated in relatively high yield.

When the process of the invention is applied to a crude extract of HBsAg from engineered yeast cells, the obtained HBsAg is bound to the non ionic detergent forming therewith composite micelles of a diameter of about 22 nm and it has been found that the ratio expressing the amount of non ionic detergent on the amount of proteins, total lipids and polysorbate in the polysorbate composite micelle is from 15 to 35% (w/v) when the assays are performed by colorimetric method for proteins (LOWRY), total lipids (ZOLLNER) and non ionic detergent (HUDDLESTON and ALLRED).

The composite micelles obtained by the process of the invention by using a polysorbate a non-ionic detergent are novel compounds which are also an object of this invention; they are immunogenic and can be formulated into vaccine form like classical HBsAg as it is well known in the art for hepatitis B virus vaccine preparation.

The invention is illustrated by the following examples which are not limitative of the scope of the invention.

EXAMPLE 1

Pelleted yeast cells (3850 g) of an engineered yeast strain expression HBsAg which have grown up to 30 g dry cells weight per liter of culture are suspended in 7.12 liters of $Na_2HPO_4$ solution (7.098 g/l).

This suspension is supplemented with 142.5 ml 4% (w/v) EDTA solution, 38.5 ml polysorbate 20 and 385 ml isopropanol containing 2.7 g phenylmethylsulfonyl fluoride (PMSF). The pH is adjusted to 8.1 ($\pm 0.1$) with NaOH (10% w/v in water). The suspension is refrigerated in an ice bath and disrupted by 2 passages through a cooled glass beads homogenizer. The homogenate (crude extract) is then centrifuged for 30 minutes at 13000 g.

PEG 400 (2.5 l) is slowly added with stirring to the crude extract (77 l) which is maintained below 15° C. The pH is then adjusted to 6 ($\pm 0.1$) by addition of acetic acid (5M) and the medium is stored for one hour at 4° C. before being centrifuged at 7,400-11,000 g for 45 minutes.

The supernatant is brought to pH 7.0 ($\pm 0.05$) with N NaOH and 300 ml of M $CaCl_2$ chloride (i.e. 30 ml per liter of supernatant) is added thereto. The pH is readjusted to 7 ($\pm 0.05$) with N NaOH and stored overnight at 4° C. The suspension is centrifuged at 3600 g for 45 minutes and the supernatant is ultrafiltered in an AMICON DC (apparatus sold by AMICON CORP., DANVERS, MA, USA)) equipped with a cartridge having a cut-off of 100,000 daltons and thereby first concentrated up to ¼ (1500 ml) of its initial volume. The solution is then washed continuously with 12.5 l of 10 mM trometamol adjusted to pH 8 ($\pm 0.1$) by addition of N hydrochloric acid (this buffer is hereafter referred to as trometamol pH 8) and supplemented with PMSF (1 mM), isopropanol (2.5% v/v) and EDTA (2 mM) (final concentrations). The retentate is then further concentrated to 350 ml.

The concentrated solution is applied to a column ($\phi 10$ cm $\times$ 100 cm) containing 7 l of FRACTOGEL® TSK HW65(F) (a semi-rigid gel consisting of hydrophilic vinyl polymers with numerous hydroxyl groups on the matrix surface with particle size 32-63 um manufactured and sold by E. Merck, Darmstadt, FRG) equilibrated in trometamol/HCl buffer 10 mM pH 7 ($\pm 0.01$) supplemented with 5% (v/v) ethylene glycol.

The HBsAg antigen containing peak is applied to a column ($\phi 5$ cm $\times$ 30 cm) of 300 ml of FRACTOGEL® TSK DEAE 650 (M) (a weakly basic anion exchanger wherein diethylaminoethyl groups are bound to the hydroxyl groups of FRACTOGEL TSK HW-65 matrix via ether linkages, manufactured and sold by E. Merck, Darmstadt, FRG) equilibrated in trometamol pH 8 at 4° C. The column is washed with trometamol pH 8 containing 005M NaCl and NBsAg is eluted with 0.15M NaCl in trometamol pH 8.

The eluate is applied to a column of FRACTOGEL® TSK HW65(F) equilibrated with $Na_2HPO_4/NaH_2PO_4$ buffer (10 mM) pH 6.8 supplemented with NaCl (150 mM) yielding a solution of HBsAg/polysorbate composite micelles.

The purification level obtained at each stage of the purification is shown in Table I.

TABLE I

| Fraction | Vol (l) | Total HBsAg by RIA (mg) | Total Proteins (g) | Total Polysaccharides (g) | Total Nucleic acids (g) | Total lipids (g) |
|---|---|---|---|---|---|---|
| Crude extract | 7.7 | 1232 | 259 | 114 | 32.5 | 104 |
| PEG supernatant | 8.02 | 1100 | 64 | 9.5 | 641 | 53.7 |
| $CaCl_2$ supernatant | 8 | 1190 | 37 | 3.8 | 512 | 27.2 |
| Retentate | .350 | 1320 | 26.7 | .744 | 37.6 | 3.596 |
| HBsAg peak TSK | 1.06 | 736 | .935 | .014 | 16 | .352 |
| Eluate TSK- | .15 | 722 | .428 | .0084 | 2.6 | .275 |

TABLE I-continued

| Fraction | Vol (l) | Total HBsAg by RIA (mg) | Total Proteins (g) | Total Polysaccharides (g) | Total Nucleic acids (g) | Total lipids (g) |
|---|---|---|---|---|---|---|
| DEAE HBsAg Peak TSK | .45 | 1117 | .244 | .0094 | 2.0 | .179 |

RIA: Radio Immuno Assay

The following Table II summarizes the composition of composite micelles of 3 different vaccine batches obtained by the above process with polysorbate 20.

TABLE II

| Batch | Proteins ($\mu$g/ml) (A) | Total Lipids ($\mu$g/ml) (B) | Polysorbate 20 ($\mu$g/ml) (C) | Ratio $\frac{C}{A/B/C}$ |
|---|---|---|---|---|
| I | 20 | 20 | 8.5 | 18 |
| II | 20 | 16 | 8.4 | 19 |
| III | 20 | 14.5 | 15.6 | 31 |

EXAMPLE 2

PEG 400 (882 ml) is slowly added to 2,650 l of crude extract prepared as described in example 1 and the pH is adjusted to 6. ($\pm$0.1). The medium is maintained at 4° C. for one hour and then centrifuged at 7400 g. The supernatant is concentrated to 1000 ml on an AMICON DC equipped with a cartridge having a cut-off of 100,000 daltons and then washed with 3 volumes of 20 mM trometamol pH 8. Powdered ammonium sulfate (277 g) is then added slowly to the retentate, under stirring and at 4° C. After 1 hour at 4° C., the precipitate is centrifuged for 15 min. at 1000 g. The supernatant is discarded and the precipitate is dissolved in 400 ml 20 mM trometamol pH 8 supplemented with 1 mM PMSF. The solution is ultrafiltered on an Amicon DC equipped with a cartridge having a cut-off of $10^6$ daltons. The retentate (500 ml) is washed with 2 volumes of trometamol pH 8 and then applied to a column containing 300 ml of TSK-DEAE 650M Gel equilibrated with trometamol pH 8. When the passage of the sample is completed, the column is washed with 0.05M NaCl in trometamol pH 8 and a linear gradient of NaCl (0.05M-0.5M) is then applied to the column. The fraction eluted with 0.15M NaCl contains the HBsAg; it is concentrated to 50 ml in an Amicon DC equipped with a cartridge having a cut-off of 10,000 and applied to a column (50×100 cm) of Sepharose 4B-Cl (an agarose gel manufactured and sold by Pharmacia Fine Chemicals, Uppsala, Sweden) equilibrated with 20 mM trometamol pH 8 supplemented with 5% ethylene glycol, yielding a solution of HBsAg/polysorbate composite micelles.

The purification level obtained at each stage is shown in Table III.

TABLE III

| Fraction | Vol (ml) | Total HBsAg by RIA (mg) | Total Proteins (g) | Total Polysaccharides (g) | Total Nucleic acids (g) |
|---|---|---|---|---|---|
| Crude extract | 2.650 | 188 | 114.721 | 36.9 | 9.250 |
| PEG supernatant | 2.530 | 160 | 22.755 | 3.321 | .536 |
| Retentate $10^5$ | 1000 | 150 | 7.468 | .181 | .175 |
| AMS-pellet | 400 | 80.8 | 1.248 | .248 | .160 |
| Retentate $10^6$ | 1000 | 72.4 | .529 | .029 | .088 |
| Eluate | 560 | 44 | .157 | 0.073 | .003 |

TABLE III-continued

| Fraction | Vol (ml) | Total HBsAg by RIA (mg) | Total Proteins (g) | Total Polysaccharides (g) | Total Nucleic acids (g) |
|---|---|---|---|---|---|
| TSK-DEAE HBsAg peak Sepharose 4B-CL | 200 | 23 | .030 | .0003 | .00005 |

RIA: Radio Immuno Assay

EXAMPLE 3

HBsAg crude extract (2 liters) is clarified by PEG 400 as described in example 1. Powdered ammonium sulfate (AMS) (450 g) is added thereto under stirring (final concentration is 45% AMS saturation). After solubilisation of the AMS, the solution is kept at 4° C. for 3 hours at the end of which period two distinct phases are obtained which are separated in a separation funnel: a clear (yellow) upper phase (PEG 400 phase) and a clear lower phase (aqueous phase), each phase representing about ±50% of the original volume. The aqueous phase is discarded and the upper phase is ultrafiltered on a Amicon DC as described for the $CaCl_2$ supernatant in example 1. The purification procedure is then further carried out as described in example 1 yielding a solution of HBsAg/polysorbate composite micelles.

The purification level obtained at each stage is shown in Table IV.

TABLE IV

| Fraction | Vol (ml) | Total HBsAg by RIA (mg) | Total Proteins (g) | Total Polysaccharides (g) | Total Nucleic acids (g) |
|---|---|---|---|---|---|
| Crude extract | 2000 | 99 | 55.000 | 22.000 | 5.588 |
| PEG supernatant | 2000 | 92 | 13.200 | 5.680 | 243 |
| PEG phase | 1000 | 98 | 2.800 | 1.536 | 98 |
| Retentate | 50 | 98 | 1.500 | .140 | 6.66 |
| HBsAg peak TSK | 123 | 52 | .140 | .0077 | 2.84 |
| Eluate TSK-DEAE | 25 | 54 | .0377 | .0011 | .44 |
| HBsAg peak TSK | 60 | 35 | .0207 | .00154 | .39 |

RIA: Radio Immuno Assay

EXAMPLE 4

HBsAg crude extract (2 liters) is clarified by PEG 400 as described in example 1. Powdered ammonium sulfate (AMS) (450 g) is added thereto under stirring (final concentration is 45% AMS saturation). After solubilisation of the AMS, the solution is kept at 4° C. for 3 hours at the end of which period two distinct phases are obtained which are separated in a separation funnel: a clear (yellow) upper phase (PEG 400 phase) and a clear lower phase (aqueous phase), each phase representing about ±50% of the original volume. The aqueous phase is discarded and a one liter aliquot of PEG phase (upper phase) is diluted twofold with 10 mM trometamol pH 8 and applied to a column containing 300 ml of FRACTOGEL TSK-DEAE 650(M) gel equilibrated with trometamol pH 8 at a flow rate of 100 ml/hour. The gel is washed with trometamol pH 8 containing 0.05M NaCl and the HBsAg is then eluted with a NaCl gradient (0.05-0.5M NaCl in trometamol pH 8). A HBsAg peak is eluted with 0.15M NaCl and, after concentration in an AMICON DC equipped with a cartridge having a cutoff of 10,000, the retentate is applied to a column (5×100 cm) of Sepharose 4B-Cl equilibrated with trometamol pH 8 containing 5% (v/v) ethylene glycol, yielding a peak of HBsAg/polysorbate composite micelles.

The purification level at each stage is shown in Table V.

TABLE V

| Fraction | Vol (ml) | Total HBsAg by RIA (mg) | Total Proteins (g) | Total Polysaccharides (g) | Total Nucleic acids (g) |
|---|---|---|---|---|---|
| Crude extract | 2100 | 200 | 60.600 | 19.000 | 4.860 |
| PEG phase | 1200 | 210 | 3.100 | 1.436 | 80 |
| Eluate TSK-DEAE | 460 | 134 | .750 | .0048 | 05 |
| HBsAg peak Sepharose 4B-CL | 150 | 110 | .120 | .0014 | 0.3 |

RIA: Radio Immuno Assay

EXAMPLE 5

HBsAg crude extract (500 ml) is clarified by slow addition of a solution of 50 g PEG 6000 in 160 ml of water under stirring at 4°. The pH is adjusted to 6.1 by addition of 5M acetic acid. After a one hour storage at 4°, the extract is centrifuged for 15 min. at 7000 g. Powdered ammonium sulfate (157 g) is then added to the supernatant under stirring (final concentration is 50% in saturated ammonium sulfate). After solubilisation, the solution is kept at 4° C. for 3 hours, after which period two distinct phases are obtained which are separated in a separation funnel. The upper phase (PEG phase containing the HBsAg) is diluted twofold with trometamol pH 8 and then applied to a column containing 300 ml of TSK-DEAE 650(M) gel equilibrated in trometamol pH 8 at a flow rate of 100 ml/hour. The gel is washed with trometamol pH 8 containing 0.05M NaCl and the HBsAg antigen is eluted with trometamol pH 8 containing 0.15M NaCl, concentrated in an AMICON DC equipped with a cartridge having cut-off of 10,000 and then applied to a 2 liters column (5 × 100 cm) of FRACTOGEL TSK-HW65 (F) equilibrated with trometamol pH 8 containing 10% (v/v) ethylene glycol, yielding a solution of HBsAg/polysorbate composite micelles.

The purification level at each stage is shown in Table VI.

TABLE VI

| Fraction | Vol (ml) | Total HBsAg by RIA (mg) | Total Proteins (g) | Total Polysaccharides (g) | Total Nucleic acids (g) |
|---|---|---|---|---|---|
| Crude extract | 500 | 123 | 22.600 | 6.400 | 1.200 |
| PEG supernatant | 490 | 100 | 4.153 | .509 | 24 |
| PEG phase | 270 | 110 | 1.820 | .2096 | 85.3 |
| Eluate TSK-DEAE | 150 | 66 | .258 | .028 | 4 |
| HBsAg peak TSK | 60 | 68 | .065 | .00048 | .084 |

RIA: Radio Immuno Assay

EXAMPLE 6

PEG 400 (13 ml) is added slowly to alpha-1-antitrypsin crude extract (120 ml) from an engineered yeast culture and the pH is adjusted to 6.1 with 5M acetic acid. After a one hour storage at 4° C., the medium is centrifuged at 5000 g for 15 minutes and 1M CaCl$_2$ solution is added slowly to a final concentration of 40 mM. The pH is adjusted to 7 with 1M NaOH and, after overnight storage at 4° C., the medium is centrifuged at 7000 g for 15 minutes. The supernatant is diluted twofold with 50 mM trometamol adjusted to pH 8.7 by addition of 0.1N hydrochloric acid and applied to a column of FRACTOGEL TSK-DEAE 650(M) (20 ml) equilibrated with 50 mM trometamol pH 8.7 prepared as indicated above but supplemented with 5 mM mercaptoethanol. The column is washed with trometamol pH 8.7 as indicated above but supplemented with 10 mM NaCl, a NaCl gradient is applied (10 mM–250 mM) and the alpha-1-antitrypsin is eluted at a NaCl concentration of 124 mM, separated from a protein peak eluted at 80 mM NaCl. The alpha-1-antitrypsin peak is concentrated in an AMICON DC equipped with a cartridged having a cut-off of 10,000 and applied to a Sephadex 150 column equilibrated in 50 mM trometamol pH 8.7 prepared as indicated above, yielding a solution of purified alpha-1-antitrypsin.

The purification level obtained at each stage is shown in Table VI.

TABLE VI

| Fraction | Vol (ml) | Total AAT by ELISA (mg) | Total Proteins (g) | Total Polysaccharides (g) |
|---|---|---|---|---|
| Crude extract | 120 | 180 | 4.018 | .538 |
| PEG supernatant | 100 | 212 | 1.300 | .290 |
| CaCl$_2$ supernatant | 100 | 194 | .660 | .110 |
| Eluate TSK-DEAE | 520 | 180 | .210 | .0052 |

AAT: alpha-1-antitrypsin

EXAMPLE 7

The technique is as described in Example 1 but 300 ml of M MnCl$_2$ are substituted for the 300 ml of M CaCl$_2$ therein specified. The characteristics of the final product are similar to those of the product obtained at the end of Example 1.

EXAMPLE 8

The technique is as described in Example 1, but 20 ml of Triton X-100 (a product manufactures by Rohm and Haas; Darmstadt, FRG) are substituted for the 38.5 ml polysorbate 20 therein specified. The characteristics of the final product are similar to those of the product obtained at the end of Example 1.

EXAMPLE 9

The technique is as described in Example 1, but 38.5 ml of polysorbate 80 are substituted for the 38.5 ml of polysorbate 20 therein specified. The characteristics of the final product are similar to those of the product obtained at the end of Example 1.

EXAMPLE 10

The solution of HBsAg composite micelle obtained at the end of Example 1 is adjusted to a protein content of 10 ug per milliliter by addition of NaCl, phosphate buffer (Na$_2$HPO$_4$/NaH$_2$PO$_4$) and ALHYDROGEL ® (an aluminium hydroxide gel manufactured and sold by SUPERPHOS Export Co, Copenhagen, Denmark) up to final concentrations of 0.9% (w/v), 20 mM and 0.15% (w/v) of Al(OH/$_3$), respectively, the final pH being 6.9.

The preparation is sterilized and distributed into 2 ml glass vials, each containing one ml dosage unit of vaccine.

EXAMPLE 11

Dosage units of the vaccine of Example 10 have been administered by intramuscular route to two series of seronegative subjects in 2 successive injections, at a one month interval. Although these injections should be considered as priming administration which should be followed by a booster, e.g. 2 months after the first injection, positive antibody responses were already noticed one and two months respectively after the first administration.

In the first series (comprising 32 seronegative subjects) one month after the first administration, the seroconversion rate was 20/32, i.e. 62.5% with a geometric mean titre (GMT) of 9.95 milli international units (MIU) and one month after the second administration the seroconversion rate was 31/32 i.e. 96.9% with GMT 36 MIU.

In the second series (comprising 46 seronegative subjects) one month after the first administration the seroconversion rate was 31/46, i.e. 67.4% with GMT 13/6 MIU.

Recording of clinical signs and symptoms revealed no temperature rise and no noticeable local reaction among the vaccinees.

What we claim is:

1. In a method for extracting and purifying a cell-bound protein from the supernatant of engineered yeast cells having produced such protein and disrupted in the presence of a non-ionic detergent, a process which comprises, as a first step, adjusting the pH of the supernatant to 6 ($\pm 0.1$), adding thereto either liquid or solid polyethylene glycol up to clarification of said supernatant, and, as a second step, treating the clarified supernatant either with a bivalent metal cation or, before ultrafiltration or after eventual ultrafiltration, with ammonium sulfate for separating said protein.

2. The process of claim 1 wherein liquid polyethylene glycol is added at a final concentration comprised between 10 and 35% (v/v).

3. The process of claim 1 wherein solid polyethylene glycol is added at a final concentration comprised between 6 and 12% (w/v).

4. The process of claim 1 wherein the protein is hepatitis B surface antigen.

5. The process of claim 2 wherein the protein is hepatitis B surface antigen.

6. The process of claim 3 wherein the protein is hepatitis B surface antigen.

7. The process of claim 1 wherein the protein is alpha-1-antitrypsin.

8. The process of claim 2 wherein the protein is alpha-1-antitrypsin.

9. The process of claim 3 wherein the protein is alpha-1-antitrypsin.

10. A process according to any of claims 1 to 9 wherein the clarified supernatant is treated with a bivalent metal cation which is calcium or manganese cation.

11. The process of claim 10 further comprising separation of the precipitate, ultrafiltration of the solution, gel permeation of the retentate, ion exchange chromatography of the protein containing peak and, eventually, a second gel permeation.

12. A process according to any of claims 1 to 9 wherein the clarified supernatant is treated with ammonium sulfate up to 40–50% saturation and isolating the purified protein in the polyethylene glycol phase.

13. The process of claim 12 wherein the polyethylene glycol phase is further subjected to eventual ultrafiltration followed by gel permeation and ion exchange chromatography.

14. The process of claim 12 wherein the polyethylene glycol phase is further subjected to eventual ultrafiltration followed by ion exchange chromatography and gel permeation.

15. The process of claim 2 wherein the clarified supernatant is subjected to ultrafiltration and the retentate is treated with ammonium sulfate up to 40–50% saturation in order to precipitate the protein which is taken over in an adequate buffer.

16. The process of claim 15 further comprising ultrafiltration, gel permeation and ion exchange chromatography.

17. A method according to any of claim 1 to 9 wherein the non-ionic detergent is a polysorbate.

18. The method of claim 17 wherein the polysorbate is polysorbate 20.

* * * * *